(12) United States Patent
Rendahl et al.

(10) Patent No.: US 6,757,607 B2
(45) Date of Patent: Jun. 29, 2004

(54) AUDIT VEHICLE AND AUDIT METHOD FOR REMOTE EMISSIONS SENSING

(75) Inventors: Craig S. Rendahl, Tucson, AZ (US);
John DiDomenico, Tucson, AZ (US);
Ronald J. McNeill, Tucson, AZ (US);
Robert A. Gentala, Tucson, AZ (US)

(73) Assignee: SPX Corporation, Charlotte, NC (US)

( * ) Notice: Subject to any disclaimer, the term of this patent is extended or adjusted under 35 U.S.C. 154(b) by 336 days.

(21) Appl. No.: 09/934,529

(22) Filed: Aug. 23, 2001

(65) Prior Publication Data

US 2003/0040863 A1 Feb. 27, 2003

(51) Int. Cl.⁷ .............................................. G06G 7/70
(52) U.S. Cl. .................... 701/115; 701/114; 701/108
(58) Field of Search ............................. 701/100, 103, 701/108, 114, 115, 29; 123/527

(56) References Cited

U.S. PATENT DOCUMENTS

| | | | |
|---|---|---|---|
| 3,696,247 A | 10/1972 | McIntosh et al. | 250/83.3 H |
| 3,811,776 A | 5/1974 | Blau, Jr. | 356/51 |
| 3,957,372 A | 5/1976 | Jowett et al. | 356/51 |
| 3,958,122 A | 5/1976 | Jowett et al. | 250/346 |
| 3,973,848 A | 8/1976 | Jowett et al. | 356/51 |
| 4,012,144 A | 3/1977 | Hedelman | 356/73 |
| 4,013,260 A | 3/1977 | McClatchie et al. | 250/343 |
| 4,160,373 A | 7/1979 | Fastaia et al. | 73/23 |
| 4,171,909 A | 10/1979 | Kramer et al. | 356/73 |
| 4,204,768 A | 5/1980 | N'Guyen | 356/243 |
| 4,310,249 A | 1/1982 | Kramer | 356/414 |
| 4,348,732 A | 9/1982 | Kreft | 364/571 |
| 4,372,155 A | 2/1983 | Butler et al. | 73/114 |
| 4,390,785 A | 6/1983 | Faulhaber et al. | 250/330 |
| 4,432,316 A | 2/1984 | Ogita | 123/328 |
| 4,490,845 A | 12/1984 | Steinbruegge et al. | 382/1 |
| 4,560,873 A | 12/1985 | McGowan et al. | 250/339 |
| 4,602,160 A | 7/1986 | Mactaggart | 250/341 |
| 4,632,563 A | 12/1986 | Lord, III | 356/437 |
| 4,638,345 A | 1/1987 | Elabd et al. | 357/24 |
| 4,663,522 A | 5/1987 | Welbourn et al. | 250/223 R |
| 4,678,914 A | 7/1987 | Melrose et al. | 250/343 |
| 4,687,934 A | 8/1987 | Passaro et al. | 250/343 |
| 4,710,630 A | 12/1987 | Kuppenheimer, Jr. et al. | 250/353 |
| 4,746,218 A | 5/1988 | Lord, III | 356/437 |

(List continued on next page.)

OTHER PUBLICATIONS

Bureau of Automotive Repair; "On Road Emissions Measurement System (OREMS) Specifications"; OREMS Specifications–Version O, Jan. 28, 2002; 2002 California DCA/BAR.

Jiménez–Palacios, José Luis; "Understanding and Quantifying Motor Vehicle Emissions with Vehicle Specific Power and TILDAS Remote Sensing"; Massachusetts Institute of Technology, Feb. 1999.

Radian Corp.; "Developing an Inspection/Maintenance Program for Alternatively–Fueled Vehicles"; 1993.

Islam, Muhammed, Rendahl, Craig S., CORS, Rebecca; "Wisconsin's Remove Vehicle Emissions Sensing Study"; Final Report 1995.

(List continued on next page.)

Primary Examiner—Willis R. Wolfe
Assistant Examiner—Johnny H. Hoang
(74) Attorney, Agent, or Firm—Baker & Hostetler LLP

(57) ABSTRACT

An audit vehicle and audit method are provided for testing the performance of a remote emissions sensing system. The vehicle emits known gases. The vehicle includes a gas delivery system and senses and records telemetry information such as vehicle speed read by a sensor on a non-driven wheel, GPS information, atmospheric information, IR light information, road temperature sensing information, and gas flow rate information.

1 Claim, 6 Drawing Sheets

U.S. PATENT DOCUMENTS

| | | | |
|---|---|---|---|
| 4,795,253 A | 1/1989 | Sandridge et al. | 356/51 |
| 4,818,705 A | 4/1989 | Schneider et al. | 436/164 |
| 4,829,183 A | 5/1989 | McClatchie et al. | 250/346 |
| 4,868,622 A | 9/1989 | Shigenaka | 357/30 |
| 4,875,084 A | 10/1989 | Tohyama | 357/30 |
| 4,914,719 A | 4/1990 | Conlon et al. | 250/339 |
| 4,924,095 A | 5/1990 | Swanson, Jr. | 250/338.5 |
| 4,963,023 A | 10/1990 | Goldovsky et al. | 356/308 |
| 4,999,498 A | 3/1991 | Hunt et al. | 250/338.5 |
| 5,002,391 A | 3/1991 | Wolfrum et al. | 356/307 |
| 5,041,723 A | 8/1991 | Ishida et al. | 250/339 |
| 5,061,854 A | 10/1991 | Kroutil et al. | 250/339 |
| 5,076,699 A | 12/1991 | Ryan et al. | 356/437 |
| 5,157,288 A | 10/1992 | Hill | 307/511 |
| 5,163,412 A * | 11/1992 | Neu et al. | 123/700 |
| 5,185,648 A | 2/1993 | Baker et al. | 257/189 |
| 5,205,260 A * | 4/1993 | Takahashi et al. | 123/494 |
| 5,210,702 A | 5/1993 | Bishop et al. | 364/496 |
| 5,239,860 A | 8/1993 | Harris et al. | 73/61.48 |
| 5,252,828 A | 10/1993 | Kert et al. | 250/339 |
| 5,255,511 A | 10/1993 | Maus et al. | 60/274 |
| 5,307,626 A | 5/1994 | Maus et al. | 60/274 |
| 5,319,199 A | 6/1994 | Stedman et al. | 250/338.5 |
| 5,332,901 A | 7/1994 | Eckles et al. | 250/345 |
| 5,343,043 A | 8/1994 | Johnson | 250/338.5 |
| 5,361,171 A | 11/1994 | Bleier | 359/855 |
| 5,371,367 A | 12/1994 | DiDomenico et al. | 250/338.5 |
| 5,373,160 A | 12/1994 | Taylor | 250/338.5 |
| 5,401,967 A | 3/1995 | Stedman et al. | 250/338.5 |
| 5,416,311 A * | 5/1995 | Gran et al. | 701/117 |
| 5,418,366 A | 5/1995 | Rubin et al. | 250/338.5 |
| 5,489,777 A | 2/1996 | Stedman et al. | 250/338.5 |
| 5,498,872 A | 3/1996 | Stedman et al. | 250/338.5 |
| 5,545,897 A | 8/1996 | Jack | 250/339.13 |
| 5,583,765 A | 12/1996 | Kleehammer | 364/423.098 |
| 5,591,975 A | 1/1997 | Jack et al. | 250/338.5 |
| 5,621,166 A | 4/1997 | Butler | 73/116 |
| 5,628,296 A * | 5/1997 | Herrington et al. | 123/568.21 |
| 5,644,133 A | 7/1997 | Didomenico et al. | 250/338.5 |
| 5,719,396 A | 2/1998 | Jack et al. | 250/338.5 |
| 5,720,266 A * | 2/1998 | Nogi et al. | 123/680 |
| 5,726,450 A | 3/1998 | Peterson et al. | 250/338.5 |
| 5,797,682 A | 8/1998 | Kert et al. | 374/123 |
| 5,812,249 A | 9/1998 | Johnson et al. | 356/28 |
| 5,831,267 A | 11/1998 | Jack et al. | 250/338.5 |
| 5,922,948 A | 7/1999 | Lesko et al. | 73/117.3 |
| 6,057,923 A | 5/2000 | Sachse | 356/364 |
| 6,092,369 A * | 7/2000 | Hosogai et al. | 60/277 |
| 6,230,087 B1 | 5/2001 | Didomenico et al. | 701/29 |
| 6,307,201 B1 | 10/2001 | Didomenico et al. | 250/339.13 |
| 6,505,599 B1 * | 1/2003 | Mashiki et al. | 123/295 |

OTHER PUBLICATIONS

Walsh, P.A., Gertler, A.W.; "Texas 1996 Remote Sensing Feasibility Study"; Final Report 1997.

Popp, Peter J.; "Development of a High–Speed Ultraviolet Spectrophotometer Capable of Real–Time NO and Aromatic Hydrocarbon Detection in Vehicle Exhaust"; pp. 4–3 & 4–12;Coordinating Research Council 1997.

McVey, Iain Frederick; "Development of a Remote Sensor for Mobile Source Nitric Oxide"; University of Denver 1992.

Beaton, S.P., Bishop, G.A. and Stedman D.H.; Emissions Characteristics of Mexico City Vehicles; pp. 42, 1424–1429; Journal of Air and Waste Management Assoc. 1992.

Zhang, Yi, Stedman, Donald H., Bishop, Gary A., Beaton, Stuart P., Guenther, Paul L. and McVey, Iain F.; "Enhancement of Remote Sensing for Mobile Source Nitric Oxide"; Journal of Air & Waste Management 1996; vol. 46, pp. 25–29.

Popp, Peter John; "Remote Sensing of Nitric Oxide Emissions from Planes, Trains and Automobiles"; University of Denver 1999.

Zhang, Yi, Stedman, Donald H., Bishop, Gary A., Beaton, Stuart P., and Guenther, Paul L.; "Worldwide On–Road Vehicle Exhaust Emissions Study by Remote Sensing"; Environmental Science & Technology 1995;vol. 29#9. pp. 2286–2294.

Glover, Edward L., Mickelson, Jan and McClement Dennis; Evaluation of Methods to Determine Catalyst Efficiency in the Inspection/Maintenance Process; Society of Automotive Engineers; SAE#9600092.

Butler, James, Gierczak, Christine and Liscombe Paula; "Factors Affecting the NDIR Measurement of Exhaust Hydrocarbons"; Coordinating Research Council 1995; pp. 4–171 & 4–190.

Mackay, Gervase I., Nadler, S. Don, Karecki, David R., Schiff, Harold I., Butler, James W., Gierczak, Christine A. and Jesion, Gerald; "Final Phase 1b Report to the CRC and NREL for Research Performed Under Agreement No. VE–8–2"; Coordinating Research Council 1994.

Peterson, James E. and Stedman, Donald H.; "Find and Fix the Polluters"; Chemtech 1992, pp. 47–53.

Bishop, Gary A. and Stedman Donald H.; "Infrared Emissions and Remote Sensing"; Journal of Air and Waste Management Assoc. 1992; vol. 42#5, pp. 695–697.

Bishop, Gary A., Starkey, John R., Ihlenfeldt, Anne, Williams, Walter J. and Stedman Donald H.; "IR Long–Path Photometry: A Remote Sensing Tool for Automobile Emissions"; Analytical Chemistry 1989; vol. 61#10, pp. 671A–677A.

Axelsson, Hakan, Eilard, Anders, Emanuelsson, Annika, Galle, Bo, Edner, Hans, Regnarson Par and Kloo Henrik; "Measurement of Aromatic Hydrocarbons with the DOAS Technique"; Applied Spectroscopy 1995; vol. 49#9, pp. 1254–1260.

Baum, Marc M., Kiyomiya, Eileen S., Kumar Sasi and Lappas, Anastasios M.' "Multicomponent Remote Sensing of Vehicle Exhaust by Dispersive Absorption Spectroscopy. 1. Effect of Fuel Type and Catalyst Performance"; Environmental Science and Technology 2000; pp. 34 & 2851–2858.

Stedman, Donald H. and Smith, Dennis L.; "$NO_x$ Data by Remote Sensing"; Coordinating Research Council 1995; pp. 4–47 & 4–63.

Shore, P.R. and Devries, R.S.; "On–line Hydrocarbon Speciation Using FTIR and CI–MS"; Society of Automotive Engineers 1992; SAE #922246.

Bishop, Gary A. and Stedman, Donald H.; "On–Road Carbon Monoxide Emission Measurement Comparisons for the 1988–1989 Colorado Oxy–Fuels Program"; Environmental Science & Technology 1990; pp. 24 & 843–847.

Stedman, Donald H., Bishop, Gary, Peterson, James E., and Geunther, Paul L.; "On–Road CO Remote Sensing in the Los Angeles Basin"; CA–EPA (CARB) 1991; pp. 24 & 843–847.

x–Rite Incorporated; "A Guide to Integrating Sphere Theory and Applications"; 2002; www.labsphere.com.

Geunther, Paul L., Stedman, Donald H., Bishop, Gary A., Beaton, Stuaret P., Bean, James H. and Quine Richard W.; "A Hydrocarbon Detector for the Remote Sensing of Vehicle Exhaust Emissions"; Review of Science Instruments 1994; vol. 66(4), pp. 3024–3029.

Stephens, Robert D., Mulawa, Patricia A., Giles, Michael T., Kennedy, Kenneth G., Groblicki, Peter J. and Cadle, Steven H.; "An Experimental Evaluation of Remote Sensing–Based Hydrocarbon Measurements: A Comparison to FID Measurements"; Journal of Air and Waste Management Assoc. 1996; pp. 46 & 148–158.

Stedman, Donald H.; "Automobile Carbon Monoxide Emissions"; Environmental Science and Technology 1989; vol. 23#2, pp. 147–149.

Adachi, Masayuki, Yamagishi, Yutaka, Inoue Kaori and Ishida, Kozo; "Automotive Emissions Analyses using FTIR Spectrophotometer"; Society of Automotive Engineers 1992; SAE #920723.

Koplow, Michael D., Jimenez, Jose L., Nelson, David D., Schmidt, Stephan E.; "Characterization of On–Road Vehicle NO Emissions by Means of a TILDAS Remote Sensing Instrument"; Coordinating Research Council 1997; pp. 8–35 & 8–62.

Guenther, Paul Leonard; "Contributions to On–Road Remoter Sensing of Automobile Exhaust"; University of Denver 1992.

Cox, Frank W., Walls, John R. and Carrel, Mark W.; "Determination of Catalyst Oxidation and Reduction Efficiencies from Tailpipe Emissions Measurements"; Society of Automotive Engineers 1997; SAE #972911.

Lawson, Douglas R., Groblicki, Peter J., Stedman, Donald H., Bishop, Gary A. and Guenther Paul L.; "Emissions from In–Use Motor Vehicles in Los Angeles: A Pilot Study of Remote Sensing and the Inspection and Maintenance Program"; Journal of Air and Waste Management Assoc. 1990; vol. 40#8, pp. 1096–1105.

Stedman, Donald H., Bishop, Gary A. and Pitchford, Marc L.; "Evaluation of a Remote Sensor for Mobile Source CO Emissions"; University of Denver 1991; Rpt.#EPA 600/4–90/032.

McLaren, Scott E., Stedman, Donald H., Greenlaw, Pamela D., Bath, Raymond J., and Spear, Richard D.; "Comparison of an Open Path UV and FTIR Spectrometer"; Air and Waste Management Assoc. 1992; vol. 92–73.10.

Bishop, Gary A., Zhang, Yi, McLaren, Scott E., Guenther, Paul L., Beaton, James E., Stedman, Donald H., Duncan, John W., McArver, Alexander Q., Pierson, William R., Groblicki, Peter J., Knapp, Kenneth T., Zweidinger, Roy B. and Day, Frank J.; Enhancements of Remote Sensing for Vehicle Emissions in Tunnels; Journal of Air and Waste Management 1994; vol. 44 pp. 169–175.

McLaren, Scott E. and Stedman Donald H.; "Flux Measurements Using Simultaneous Long Path Ultraviolet and Infrared Spectroscopy"; Air and Waste Management Assoc. 1990; vol. 90–86.6.

Bishop, Gary A., McLaren, Scott E., Stedman, Donald H., Pierson, William R., Zweidinger, Roy B. and Ray, William D; "Method Comparisons of Vehicle Emissions Measurements in the Fort McHenry and Tuscarora Mountain Tunnels"; Atmospheric Environment 1996; vol. 30#12, pp. 2307–2316.

McLaren, Scott; "Open Path Spectrometers for Atmospheric Monitoring"; University of Denver 1995.

Stedman, Donald H. and Bishop, Gary A.; "An Analysis of On–Road Remote Sensing as a Tool for Automobile Emissions Control"; Illinois Dept. of Energy & Natural Resources 1990; ILENR/RE–AQ–90/05.

Stedman, Donald H., Peterson, James E. and McVey, Iain F.; "On–Road Carbon Monoxide and Hydrocarbon Remote Sensing in the Chicago Area"; Illinois Dept. of Energy & Natural Resources 1991; ILENR/RE–AQ–91/14.

Lyons, Carol E. and Stedman, Donald H.; "Remote Sensing Enhanced Motor Vehicle Emissions Control for Pollution Reduction in the Chicago Metropolitan Area: Siting and Issue Analysis"; Illinois Dept. of Energy & Natural Resources 1991; ILENR/RE–AQ–91/15.

Durbin, Thomas D., Truex, Timothy J. and Norbeck, Joseph M.; "Particulate Measurements and Emissions Characterizations of Alternative Fuel Vehicle Exhaust"; National Renewable Energy Laboratory 1998; NREL/SR–540–25741; Subcont#ACI–7–16637–01.

Didomenico, John, Johnson, Jim, Webster, Jason and Rendahl, Craig S.; "Preliminary Results from Cold Start Sensor Testing"; Coordinating Research Council 1997; pp. 4–71 & 4–72.

Stephens, Robert D. and Cadle, Steven H.; "Remote Sensing Measurements of Carbon Monoxide Emissions from On–Road Vehicles"; Journal of Air and Waste Management Assoc. 1991; vol. 41#1, pp. 39–46.

Jimenez, Jose L., McRae, Gregory J., Nelson, David D., Zahniser, Mark S. and Kolb, Charles E.; "Remote Sensing of NO and $NO_2$ Emissions from Heavy–Duty Diesel Trucks Using Tunable Diode Lasers"; Environmental Science & Technology 2000; pp. 34 & 2380–2387.

Stedman, Donald H., Bishop, Gary A., Guenther, Paul L., Peterson, James E., Beaton, Stuart P. and McVey, Iain F.; "Remote Sensing of On–Road Vehicle Emissions"; University of Denver 1992; Contract #VE–8–1.

Singer, Brett C., Harley, Robert A., Littlejohn, David, HO, Jerry and VO, Thu; "Scaling of Infrared Remote Sensor Hydrocarbon Measurements for Motor Vehicle Emission Inventory Calculations"; Environmental Science and Technology 1998; vol. 32#21, pp. 3241–3428.

Atkinson, Chris M., McKain, David L., Gautam, Mridul, El–Gazzar, Laila, Lyons, Donald W. and Clark, Nigel N.; "Speciation of Heavy Duty Diesel Engine Exhaust Emissions"; Coordinating Research Council 1995; pp. 5–71 & 5–92.

Chaney, Lucian W.; "The Remote Measurement of Traffic Generated Carbon Monoxide"; Journal of Air Pollution Control Assoc. 1983; vol. 33#3, pp. 220–222.

Todd, Michael and Barth, Michael; "The Variation of Remote Sensing Emission Measurements with Respect to Vehicle Speed and Acceleration"; Coordinating Research Council 1995; pp. 4–1 & 4–14.

Hoshizaki, H., Wood, A.D and Kemp, D.D.; "Vehicle Inspection Instrumentation"; Lockheed Missiles & Space Company 1973; ARB–3C–235–7.

Sigsby, Jr., John E., Tejada, Silvestre and Ray, William; "Volatile Organic Compound Emissions from 46 In–Use Passenger Cars"; Environmental Science & Technology 1987; pp. 21 & 466–475.

* cited by examiner

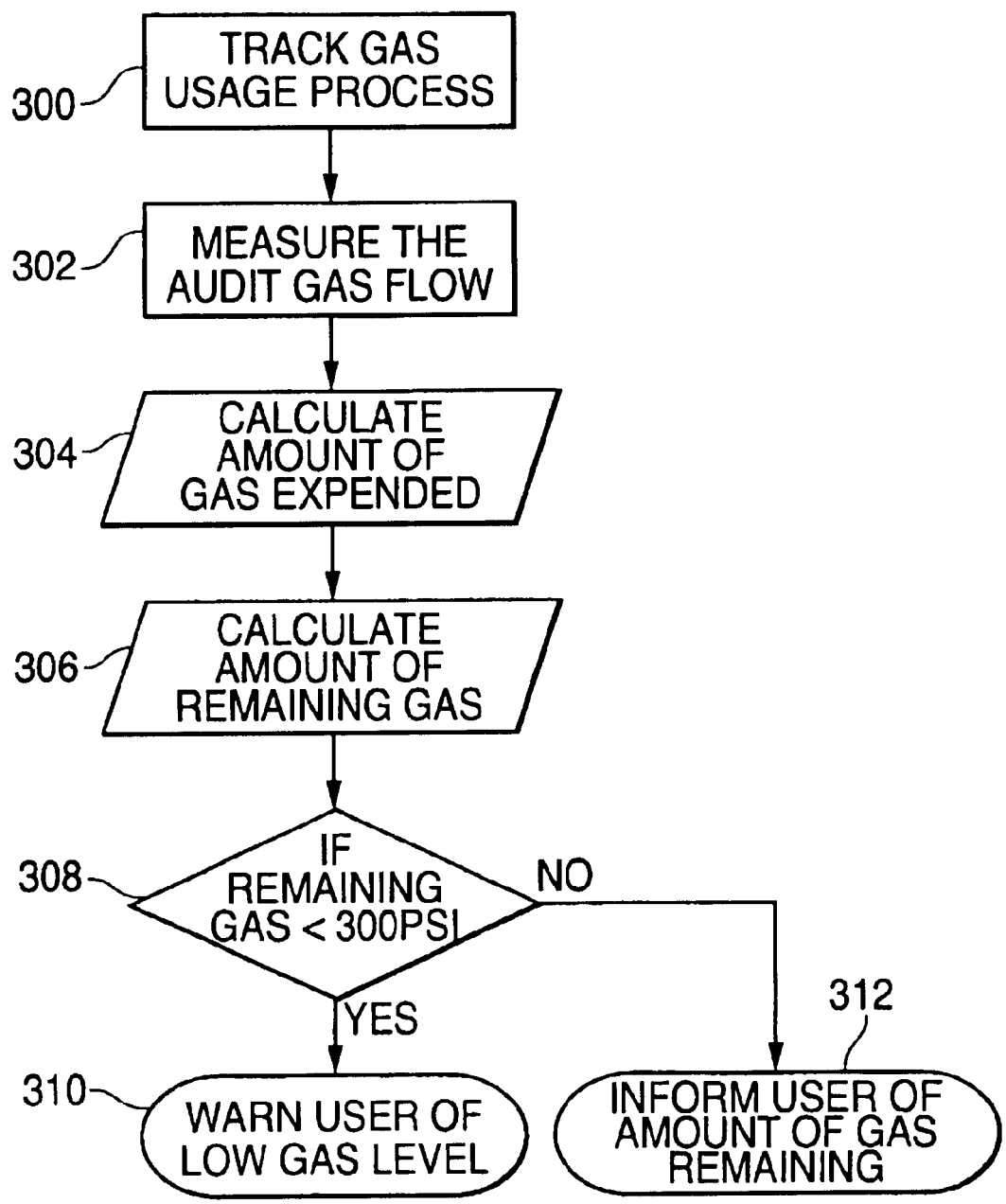

AUDIT VEHICLE AND AUDIT METHOD FOR REMOTE EMISSIONS SENSING

FIELD OF THE INVENTION

The present invention relates generally to systems and methods for auditing the performance of remote (also called open path) vehicle emissions sensing systems. More specifically, the present invention relates to an audit vehicle and audit method that can be used to drive through a remote vehicle emissions sensing system whole releasing a known quantity and mixture of gas to test the performance of the sensing system.

BACKGROUND OF THE INVENTION

Systems are known in the art for detecting the tail pipe emissions or exhaust plumes of the vehicles as they drive on a vehicle path such as a roadway. For example, it is known for a light beam to be projected across the roadway and received by a receiver that analyzes the received light and determines the components of the vehicles emissions. In order to test the performance of such systems, it is desirable to have a vehicle that emits known volumes, mixtures, and concentrations of gases and that can be driven through the sensing system in order to test the detection performance of the system.

SUMMARY OF THE INVENTION

It is therefore a feature and advantage of the present invention to provide a vehicle that emits known volumes, mixtures, and concentrations of gases and that can be driven through the system in order to test the detection performance of the system.

It is another feature and advantage of the present invention to provide a method for testing or auditing vehicle emissions sensing systems.

The above and other features and advantages are achieved through the use of a novel apparatus and method as herein disclosed. In accordance with one embodiment of the present invention, an apparatus for dispensing gas from a vehicle has a plurality of compressed gas cylinders filled with known concentrations of gases, referred to also as "gas bottles"; a plurality of shutoff valves, one valve associated with each of the gas bottle for controlling gas flow out of that gas bottle; a manifold that receives gas from each of the shutoff valves and leads to a single pressure regulator; an output gas line leading from the pressure regulator; a master shutoff valve that controls the release of the audit gas; and a sample gas outlet opening at the end of the output line with flow through the output line measured.

In accordance with another embodiment of the present invention, a system for recording telemetry data associated with a remote emissions audit vehicle, includes: a central computer; and at least one telemetry sensing device comprising at least one of: a vehicle speed sensor mounted at a non-drive wheel; a global positioning system sensor; ambient atmospheric condition sensors; an infrared beam detector; and an output gas flow rate sensor. Data from at least one sensing device is stored by the computer.

In accordance with another embodiment of the present invention, a method for recording data related to the telemetry of an audit vehicle is provided. The method includes driving the audit vehicle past a remote emissions sensor while emitting a sample blend gas; and recording telemetry data relating to the audit vehicle. The telemetry data includes at least one of: vehicle speed read by a sensor on a non-drive wheel, GPS information, atmospheric information, IR light information, road temperature sensing information, and gas flow rate information.

In another embodiment of the present invention, a method of controlling gases emitted by an audit vehicle, includes controlling a plurality of operated valves each associated with a bottle; driving the audit vehicle past a remote sensing device; and recording data related to the audit path.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 6 is a flow chart that shows a method for tracking the gas expended by an audit vehicle system.

DETAILED DESCRIPTION OF PREFERRED EMBODIMENTS OF THE INVENTION

A preferred embodiment of the present invention provides a vehicle that emits known volumes mixtures and concentrations of gases and that can be driven through the system in order to test the detection performance of the system. A preferred embodiment also provides a method for testing or auditing the performance of vehicle emissions sensing systems.

Figure 1:
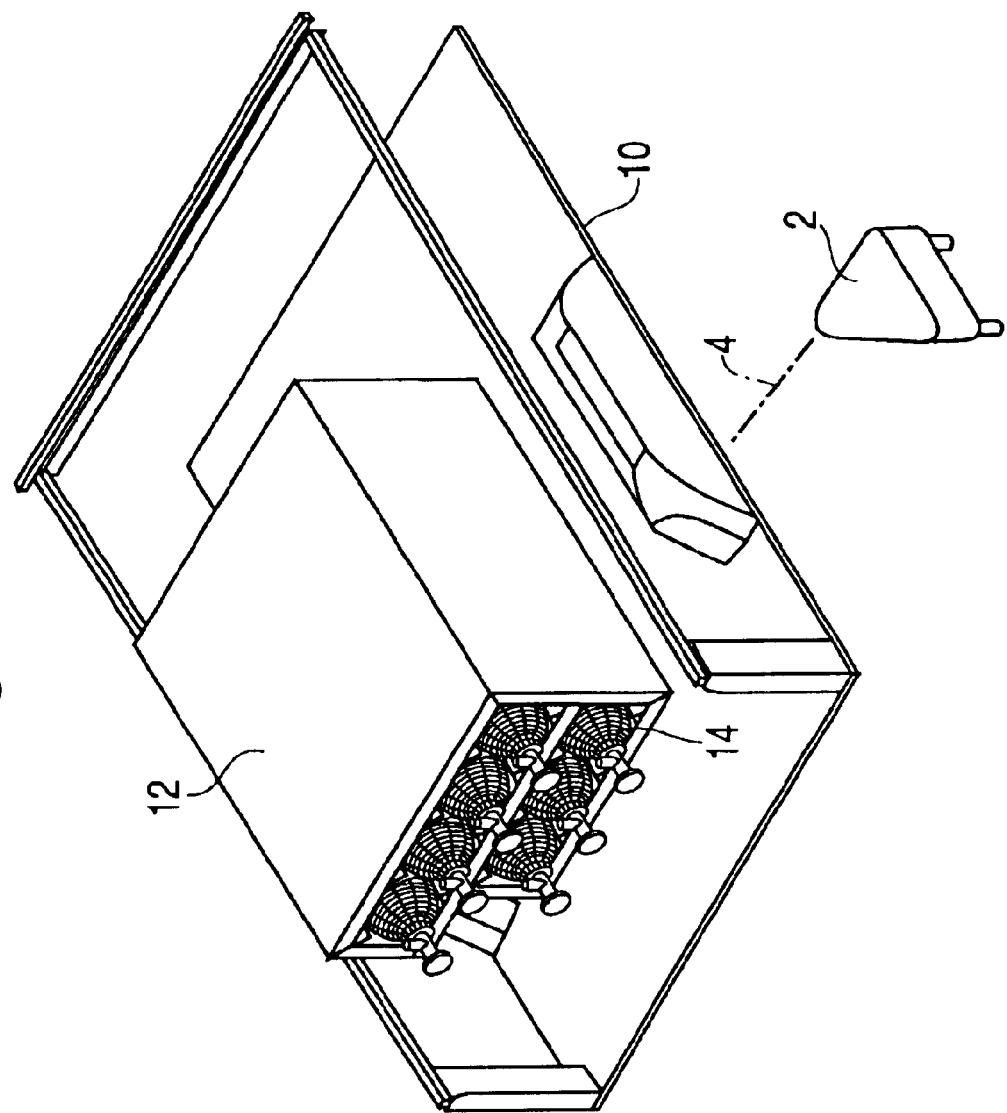
FIG. 1 is a partial respective view of a truck bed having a rack for housing sample gas bottles.
Figure 2:
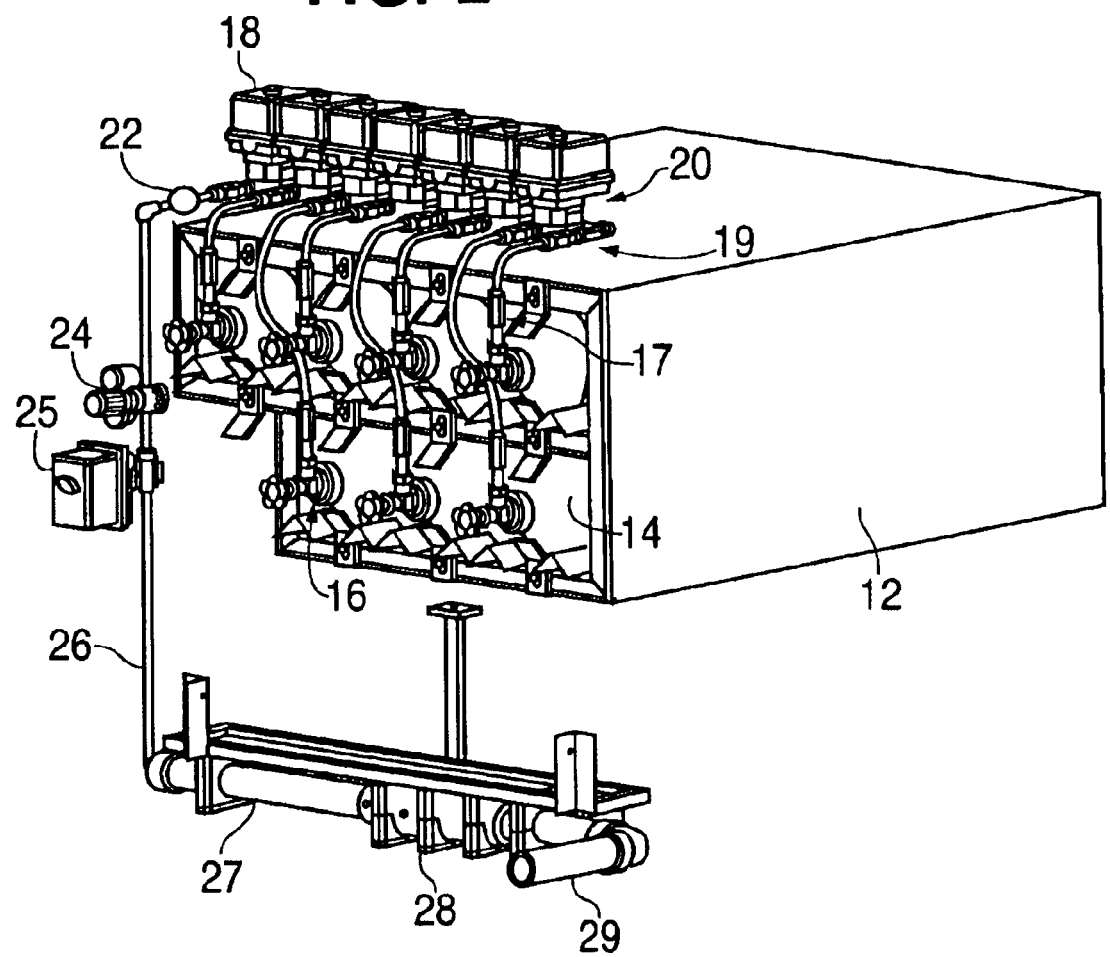
FIG. 2 is a perspective view of a rack holding sample gas bottles and a gas distribution system according to a preferred embodiment of the present invention.

A preferred embodiment of the present inventive apparatus and method is illustrated in FIGS. 1 and 2. FIG. 1 depicts a bed in the rear portion of a vehicle 10 that may be used as the audit vehicle. A remote sensing (i.e., open-path sensing)

device 2 receives a beam 4 and senses emission data when the beam 4 passes through an exhaust gas plane. The audit vehicle 10 releases bottled gas blends, while its own exhaust is diverted, to test the performance of the open path emissions sensor 2 that is sitting on the side of the road. This method of auditing the open path emissions sensor 2 that sits on the side of the road is best for emulating the entire process of a typical vehicle passing by the emissions sensor.

In a preferred embodiment, the audit vehicle 10 is a heavy duty pickup truck that has sufficient payload performance to carry the necessary equipment used in that embodiment. In the preferred embodiment, a rack 12 is provided to hold a number of compressed gas cylinders, also referred to as gas bottles 14, which in a preferred embodiment, includes seven gas bottles. These gas bottles 14 can include any appropriate number of different blends and may also include one bottle that is dedicated to a purge material (e.g. nitrogen) that can be released to purge the system of the blended gases. Each bottle contains one blend of gases. Thus, one bottle is used at a time. The purging bottle is used between different blends, that is when switching from one blend to another, to flush the system of any residual gases left over from the previously used blend.

Turning to FIG. 2, in a preferred embodiment, the rack 12 holds the gas bottles 14 as shown. Each gas bottle 14 has a primary valve 16 and outlet port as shown. A check valve 17 is also provided at the output of each bottle 14 to prevent back filling of the bottle. This check valve 17 is desirable, as it is possible for one of the bottles connected to the manifold 20 to have a higher pressure, forcing a backfill until the pressures in each bottle are the same. This backfill condition could occur if any of the shutoff valves 18 were to remain open for more than one bottle at a time. A second check valve 19 may be used between a shutoff valve 18 and the common gas manifold 20 as an additional measure of assurance in not contaminating the contents of one gas blend with another. Each gas bottle 14 has a line leading to a shutoff valve 18 as shown. In a preferred embodiment, the shutoff valve 18 is a power driven ball valve. A plunger type solenoid valve can also be used, however a ball valve provides a good ability to handle high pressures, such as up to 2000 psi in the gas cylinders, and when opened ball valves do not restrict the gas flow. In the preferred embodiment the ball valves are motorized and are controlled by a computer in the cab of the vehicle as described herein. However, in other embodiments the valves 18 can be controlled by a switch in the cab or alternatively a switch on the outside of the valve housing that can be operated by the user to open and close the valve.

An advantage of providing multiple ball valves 18, one for each tank 14, is that the operator does not have to detach and reattach a single valve each time the operator desires to change from one bottle to another. That is, in the preferred embodiment illustrated in FIG. 2 with multiple valves 18, the operator needs only to disconnect each bottle 14 from its associated line when it is time to change a bottle because it has been expended. This feature provides an ability to change between blends (that is change between bottles) very quickly while on site. Thus, in an audit environment, this reduces the time an operator spends outside the vehicle as compared to having to connect and disconnect a single valve each time it is desired to change between bottles. This benefit is enhanced by control of the ball valves remotely from inside the vehicle cab.

In normal use to output a test blend, only one of the valves 18 is open at a time, and the others are closed. A manifold 20 leading from the shutoff valves 18 and secondary check valves 19 if equipped leads to an electronic pressure sensor that leads to a pressure regulator 24 that can be set so that the test blend (or purge gas) is output with a known pressure, hence providing a control of the flow volume.

Downstream from the pressure regulator 24 is master release valve 25, preferably another motorized ball valve, which is used to activate gas flow through the remaining portion of the gas distribution system. This valve 25 can also be controlled by a central computer from inside the vehicle cab, or can manually be operated by a momentary remote switch located in the audit vehicle's cab . . . After the master release valve 25, the gas passes through a line 26 into a output pipe 27 that leads to an output opening 29. A venturi flow sensor 28 is present in a portion of the output pipe 27. This flow sensor 28 measures the flow of audit gases through the gas delivery system, by sensing the pressure differential through a venturi restriction.

Figure 3:
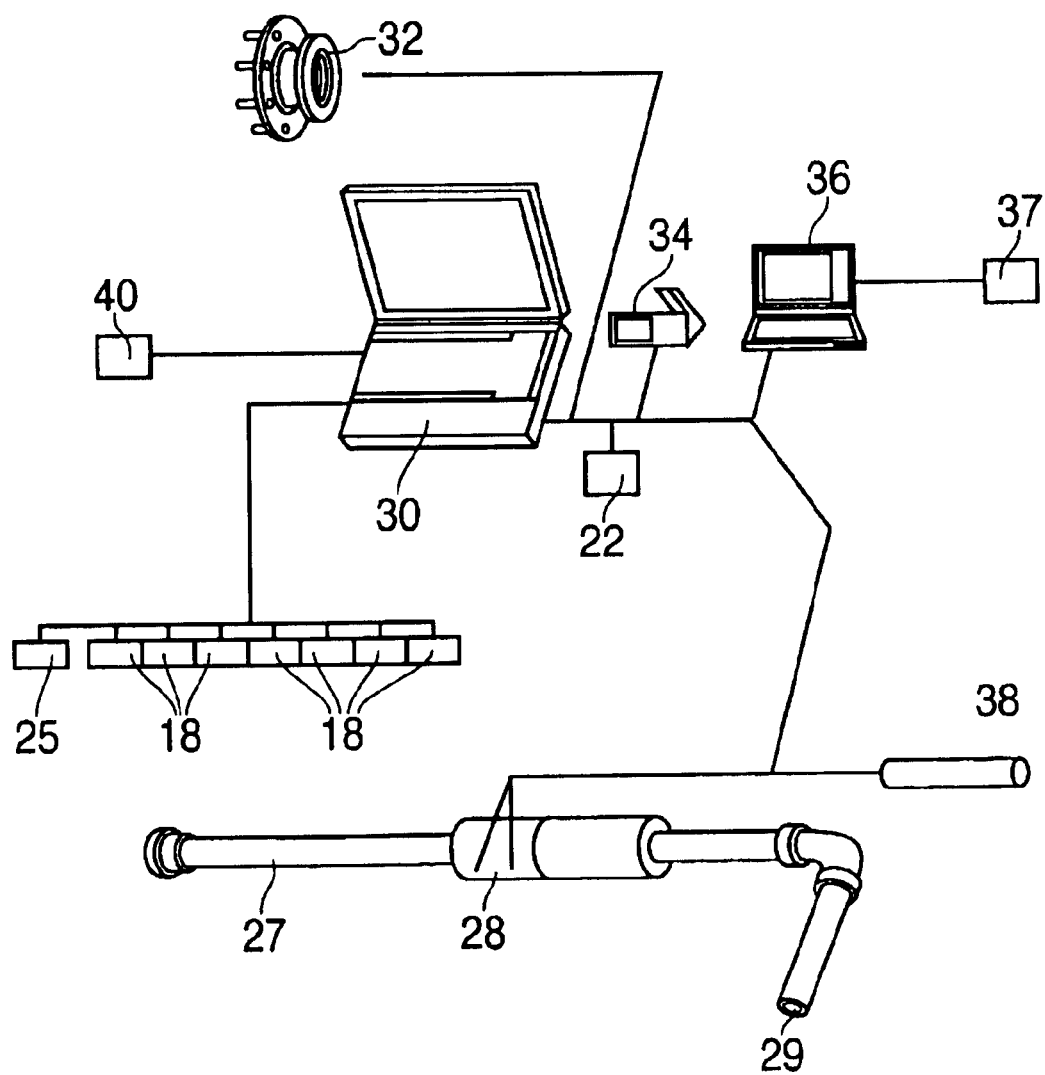
FIG. 3 is a schematic diagram illustrating a central processing computer and various peripheral devices that provide information to the computer.

FIG. 3 schematically depicts the connection of, and communication between, various components of the audit vehicle 10. The audit vehicle 10 has a computer 30, which may be a laptop computer. The computer 30 preferably runs scientific logging software as well as audit process controlling software. The computer 30 receives vehicle speed and acceleration measurements from a wheel speed sensor 32. In preferred embodiments, the wheel sensor is mounted to a non-drive wheel of the vehicle, such as for example, a front wheel of a pickup truck having only the rear wheels driven. This is to potentially avoid variations in speed caused by the audit vehicle's engine, though a drive wheel sensor could be used. A non-drive wheel is specified primarily because systems that measure vehicle speed through an apparatus that is attached to or monitors the speed of the driveshaft and related components has proven to be inconsistent in reporting speed and especially change in speed (acceleration). For this reason, a non-drive wheel is preferred, however data from a drive wheel, if the data is measured from a speed sensing device at the wheel, should not be susceptible to engine output variations, slop in the drive train, etc. that a driveshaft mounted speed measuring system would encounter. In this case it is conceivable that data collected from even a drive wheel should provide acceptable precision and accuracy of speed and change of speed measurements. The sensor 32 can be an antilock brake wheel speed sensor. The taking of data from a speed sensor on a front wheel has been found to have advantages as compared to speed sensor that is mounted on a drive shaft because driven components such as a drive shaft or differential are subject to speed fluctuations caused by the vehicle's engine or loose tolerances in the various parts of the drive train. Non-drive wheels have been found not to be subject to the same fluctuations, and hence to provide a truer and steady indication of actual vehicle speed. Speed information from the sensor 32 is fed into the central computer 30 and is monitored so that the speed at which the audit test was conducted can be verified upon later examination. Audit runs are to be conducted within a range of speed, however the speed data will be used to audit any speed measuring devices that accompany the emissions sensor 2. The computer 30 also calculates change in speed, i.e. acceleration, from information collected from the speed sensor 32, and records this calculated acceleration along with the measured speed.

Also providing an input signal to the computer 30 is a GPS receiver 34. The GPS receiver 34 can provide positional data that is stored by the computer, indicating the location at which the audit was performed. Further, GPS systems have been found to have an ability to also provide an indication of vehicle speed. This indication of vehicle speed can be used to compare with the wheel sensor data for sensor 32 to ensure accuracy. Further, the GPS system 34 also provides an indication of the date and time at which testing takes place, which date and time information can be stored in the central computer 30 along with other data records to show the location date and time and speed at which test took place.

Also attached to the computer 30 is a weather module 36, for sensing ambient condition via a pod of sensors 37. The ambient condition sensors 37 detect ambient conditions such as outdoor temperature, relative humidity and/or dew point, and barometric pressure when the audit test is performed. The sensors 37 can also record road surface temperature. This information is stored by the central computer 30 and can be used to ensure that testing is done within a prescribed condition range, or to adjust the results based on ambient conditions if desired.

Accordingly, the central computer 30 can store a telemetry log which includes e.g., location, vehicle speed, ambient conditions, read temperature and the date and time for each test.

The computer 30 also receives data from an infrared (IR) pulse sensor 38 mounted on the outside of or underneath the vehicle. The remote emissions sensing system 2 projects an infrared beam 4. As the vehicle 10 is driven past the sensing system during an audit run, the IR sensor 38 detects the beam (and correspondingly detects that the vehicle has just passed the emissions sensor). The IR sensor 38 sends a pulse signal to the computer 30. This pulse signal indicates the referenced time at which the vehicle passed the emissions sensor, and can be used for several purposes. First, the time of the pulse is stored by the computer, and thus the computer can store the other telemetry data corresponding to that time. Further, since the GPS unit 34 gathers date & time data from potentially the same source as the remote emissions sensing system 2 (if equipped with a GPS that supplies date & time among other information), the time clocks of both the audit vehicle computer 30 and the remote emissions sensing system 2 will be synchronized.

FIG. 3 also shows that the computer 30 can control the shutoff valve 18 and master release valve 25. This permits the selection of gases from a remote location, rather than the operator needing to manually turn valves or move components to the rear of the vehicle. Of course, in other embodiments, the valves could be controlled remotely in another fashion, or could be activated manually if necessary.

A power inverter 40 can be provided to take power from the audit vehicle and invert from 12 volts DC to 110 volts AC it so that it is compatible with any of the pieces of the equipment, such as computer 30, GPS 34, and weather monitor 36 as necessary.

The computer 30 also receives information from a flow rate detector in the output pipe 27 and from a pressure transducer mounted in the gas manifold 22. The detector is a venturi gas flow measurement system 28 that provides gas flow measurements to an adequate degree of precision and accuracy The flow detector 28 can be used for test accuracy and also to indicate when a gas bottle is nearly empty. The pressure transducer 22 supplies data logged by the computer 30 regarding delivery pressure to the master release valve 25 and can be cross-verified with the pressure gage on the mater regulator 24.

The computer 30 can also receive data from a vehicle's standard on-board diagnostic system (e.g., OBD), if such data is desired. The OBD system can provide engine RPM, load on engine, and other parameters useful in quality assuring the information gathered from speed sensor 32 and measured weather parameters gathered by the weather module 36.

Figure 4:
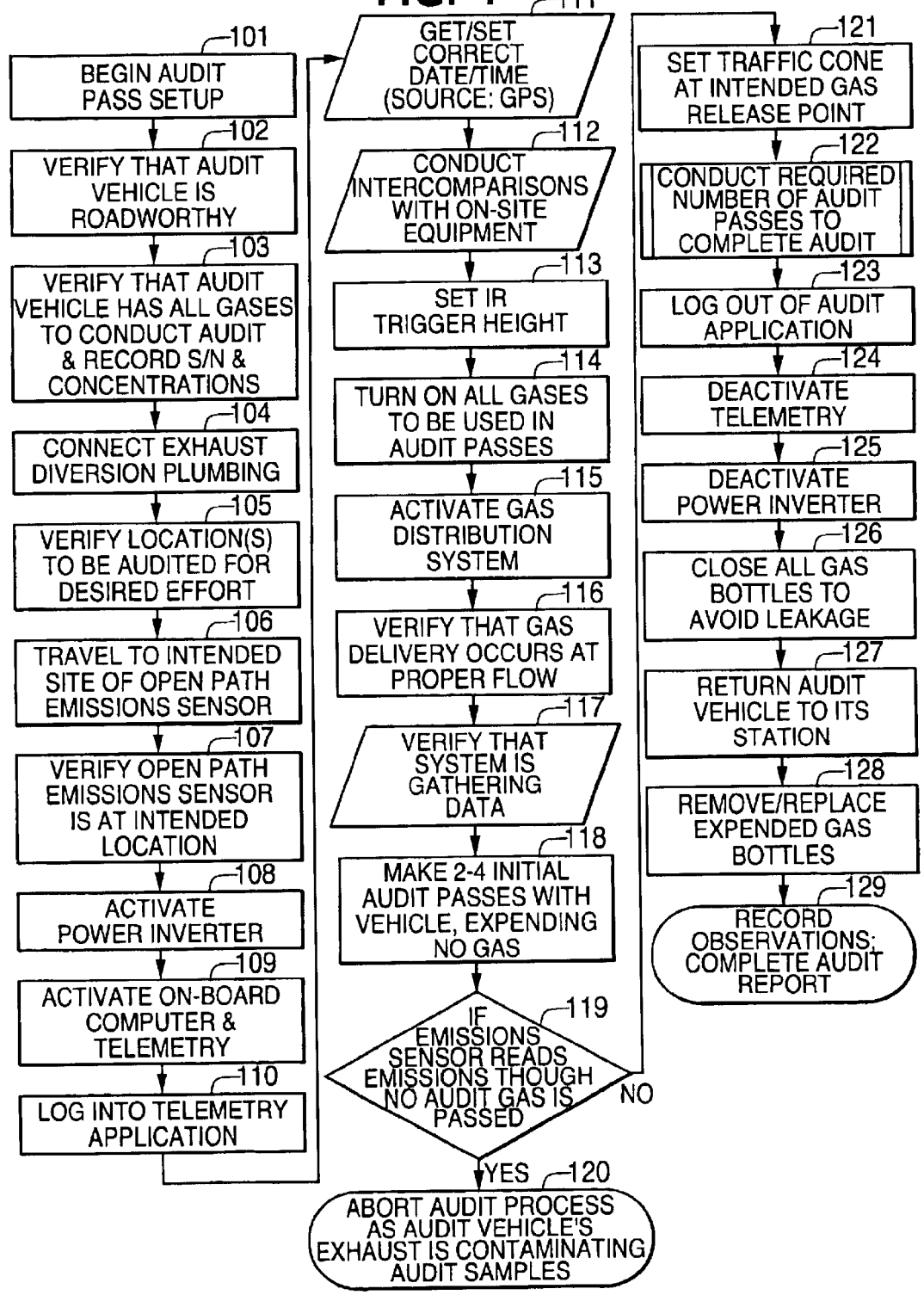
FIG. 4 is a flow chart showing a series of steps that is performed during an audit sequence.

FIG. 4 is a flow chart that depicts an overall audit process. At step 101, the user decides to initiate an audit. At step 102, the user verifies that the audit vehicle is road worthy by visually and otherwise checking the vehicle systems. This includes verifying that the audit vehicle has enough fuel to complete the day's auditing activities. At step 103, the user verifies that the audit vehicle has the appropriate gases and records identifying information, such as gas cylinder serial number and certified concentrations, in a special auditing log or in an electronic log contained within computer 30.

At step 104, the user connects exhaust diversion plumbing on the vehicle. In a preferred embodiment of the vehicle 10, the vehicle 10 is a conventional vehicle pickup truck, which has an exhaust diverting device mounted to it. The exhaust diverting device is a vertical stack that has an sufficiently high so that it will not interfere with measurement of an sample gas plume near the ground. The diverting device connects to the vehicle's exhaust system, sending the exhaust gases high above the roofline of the vehicle to assure that audit vehicle's exhaust gases do not contaminate the gases being released out the output pipe 29 from the audit gas bottles 14. A second, dummy tail pipe, which comprises the outlet pipe 27, flow measurement system 28, and outlet 29, is also mounted to the lower rear of the vehicle and it is from where the audit gases are released during an audit run.

At step 105 the operator verifies the location where the open path emissions sensor 2 is sited. At step 106, the operator travels to the audit site. At step 107, the operator verifies that the open path emission sensor 2 is at the audit site. At step 108, the operator activates a power inverter, which powers equipment such as for example, the computer 30. At step 109, the operator activates the on board computer 30 and its associated telemetry sensing devices 22, 34, 36, 38 and 28. At step 110 the operator logs the computer 30 into a telemetry software application. At step 111, the operator insures that the computer 30 is using the correct date and time which may be provided from the GPS unit 34. At step 112, the operator conducts an intercomparison between the audit vehicle's weather measuring equipment and the on site equipment located within or near the open path emissions sensor 2. GPS location data 34 should also be compered with that in the emissions sensor 2. At step 113, the operator sets and/or checks the height of the infrared (IR) beam detector 38 that senses the IR source of the emissions sensor's 2 optical path 4, which will trigger the IR detector 38 to identify the exact time at which the vehicle passes the open path sensing equipment. At step 114, the operator opens the primary valves 16 of each bottle. At step 115, the operator activates each of the shutoff valves 18 and master release valve 25 and verifies that gas delivery is occurring at a proper flow. The bottle of purge gas is preferably left to last in the sequence of checking the delivery of gases so that the entire gas delivery system is purges of any concentrations of audit gases. At step 117, the operator verifies that the computer 30 is gathering telemetry data. At step 118, the operator makes two to four audit passes with the vehicle expending no gas. This is done to verify that the audit vehicle's engine emissions are properly diverted high over the emissions sensor 2 optical path 4. At step 119, the operator checks if the emissions sensor 2 is reading emissions even though no audit gas was passed. If so, at step 120, the operator aborts the audit process because there will be contamination of audit gases by the audit vehicle's own emissions. At step 121, the operator sets a traffic cone to indicate an intended gas release start point. This provides for a consistent point of release of the audit gases by the master release valve 25. At step 122, the operator conducts a required number of audit passes to perform an audit.

At step 123 the operator logs the computer 30 out of the audit application. At step 124, the operator deactivates the telemetry devices 22, 34, 36, 38 and 28. At step 125, the operator deactivates the power inverter 40 to avoid running down the battery in the audit vehicle. At step 126, the operator closes all gas bottles by closing each primary valve 16 to avoid leakage. At step 127 the operator returns the audit vehicle 10 to its storage location. At step 128, the operator can remove and/or replace any expended gas bottles 14. At step 129 the operator can record observations and complete an audit report including telemetry information from the computer 30 and emissions data read by the emissions sensor 2 if available at the end of the auditing activities.

Figure 5:
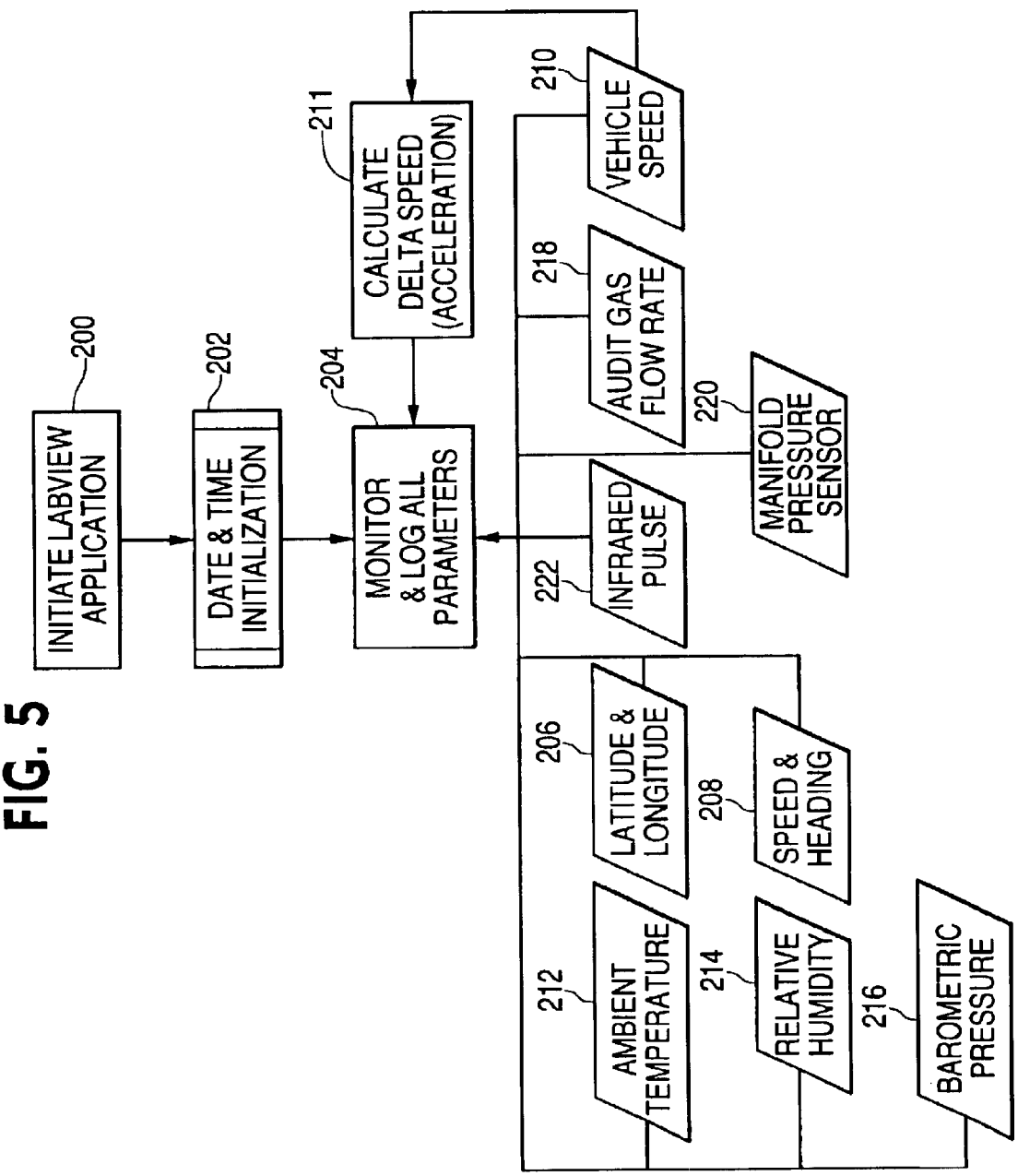
FIG. 5 is a flow chart showing various information that is monitored and logged by the computer.

FIG. 5 is a flow chart depicting various information processed by the telemetry system in the computer 30. The software application is initiated at step 200, and the date and time is initialized at step 202 from the GPS 34. Then, at step 204 the system monitors and logs the parameters including e.g., ambient temperature 212, relative humidity 214, barometric pressure 216 from weather module 36 and pod of sensors 37. Latitude and longitude 206, speed and heading 208 data are gathered from the GPS unit 34., The telemetry system also records a pulse 222 when the infrared sensor 38 senses the sample path 4 of the emissions sensor 2. Audit gas flow rate 218 from gas flow sensor 28, and the gas manifold pressure 220 collected from the pressure transducer 22 in the gas manifold 20 are recorded regardless of whether audit gas is released. The computer 30 calculates acceleration 211 from a change in vehicle speed 210 measured by the wheel sensor 32.

FIG. 6 shows a feature of a preferred embodiment the invention that tracks gas usage process when initialized in step 300. The system measures the audit gas flow 302 via the gas flow sensor 28. The system calculates the amount of gas expended from each bottle at step 304 in the computer 30 and calculates the remaining amount of gas at step 306. At step 308, if the remaining gas is less than a predetermined value, the system warns the user of a low gas level at 310, or informs the user of the amount of gas remaining at step 312, if the remaining gas is more than the predetermined value. This system is effective in tracking the amount of remaining audit gas left in cylinders 14, because the amount of gas originally loaded into the cylinders is provided by the vendor of the gases. The original amount of gas must be entered into the computer 30 in order for accurate gas usage information to be available.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for recording telemetry data associated with a remote emissions audit vehicle, the system comprising:

a plurality of compressed gas cylinders;

a plurality of shutoff valves, one valve associated with each of the gas cylinders for controlling gas flow out of the gas cylinders;

a check valve on at least one of the gas cylinders that prevents gases from flowing back into the gas cylinder;

a manifold that receives gas from each of the primary valves and leads to a pressure regulator;

an output gas line leading from the pressure regulator;

a sample gas outlet opening at the end of the output line;

a central computer;

at least one telemetry sensing device comprising at least one of:
  a vehicle speed sensor mounted at a wheel of the audit vehicle;
  a global positioning system sensor;
  an ambient atmospheric condition sensor;
  an infrared beam detector; and
  a pressure transducer used to measure pressure in a gas delivery manifold;

wherein data from at least one telemetry sensing device is stored by the computer; and a flow rate detector in communication with the central computer that is used to determine the gas flow out of the gas cylinder and indicates when the gas cylinder is nearly empty.

* * * * *